(12) United States Patent
Chaplin et al.

(10) Patent No.: US 6,346,618 B1
(45) Date of Patent: Feb. 12, 2002

(54) OPTICAL RESOLUTION OF NARWEDINE-TYPE COMPOUNDS

(75) Inventors: David Andrew Chaplin; Nicholas Bernard Johnson; Gerard Andrew Potter; Jane Marie Paul, all of Cambridge (GB)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 09/194,332

(22) PCT Filed: May 23, 1997

(86) PCT No.: PCT/GB97/01425
§ 371 Date: Jun. 28, 1999
§ 102(e) Date: Jun. 28, 1999

(87) PCT Pub. No.: WO97/45431
PCT Pub. Date: Dec. 4, 1997

(30) Foreign Application Priority Data

May 24, 1996 (GB) .............................. 9610887

(51) Int. Cl.⁷ ........................................... C07D 223/00
(52) U.S. Cl. ..................................................... 540/581
(58) Field of Search ........................................ 540/581

(56) References Cited

U.S. PATENT DOCUMENTS 6,043,359 A  *  3/2000  Czollner et al. ............ 540/581

* cited by examiner

Primary Examiner—Brenda Coleman
(74) Attorney, Agent, or Firm—Saliwanchik, Lloyd & Saliwanchik

(57) ABSTRACT

A process for the asymmetric transformation of a racemic compound of formula (I) wherein $R_1$ is H or a alkyl group having up to 20 carbon atoms, $R_2$ is H, or an alkyl, aryl, alkaryl or aralkyl group having up to 20 carbon atoms, and X is H, a halogen atom, tert-butyl, or any other removable substituent, comprises reaction of racemic compound (I) with an enantiomerically-enriched acid $HY^*$, wherein $Y^*$ is a chiral group, to form a diastereomeric salt of compound (I) having $Y^*$ as a counterion. The salt obtained can then be reduced to give enantiomerically-enriched galanthamine, or a derivative thereof.

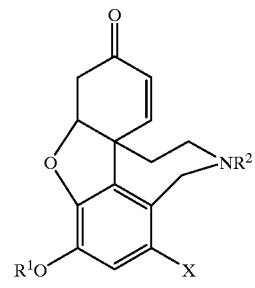

30 Claims, No Drawings

OPTICAL RESOLUTION OF NARWEDINE-TYPE COMPOUNDS

CROSS-REFERENCE TO A RELATED APPLICATION

This application is a national stage entry under 35 U.S.C §371 of PCT/GB97/01425, filed May 23, 1997.

FIELD OF THE INVENTION

This invention relates to a crystallisation-induced asymmetric transformation, or dynamic resolution, of narwedine-type compounds, and reduction of the resulting diastereomeric salts to galanthamine-type compounds.

BACKGROUND TO THE INVENTION (−)-Galanthamine is an amaryllidaceae alkaloid which is currently under investigation for the treatment of Alzheimer's disease. Galanthamine is extracted from daffodil bulbs, a process both expensive and time consuming. (−)-Galanthamine has been synthesised by resolution of narwedine to obtain (−)-narwedine, and subsequent reduction to (−)-galanthamine.

Barton and Kirby, J. Chem. Soc. (1962) 806, disclose the first synthetic route to (−)-galanthamine from racemic narwedine which had been prepared in very low yield from N-(3-hydroxy-4-methoxy-benzyl)-N-methyl-2-(4-hydroxyphenyl)-ethylamine. They found that (−)-narwedine crystallised preferentially when (+)-galanthamine or a mixture of (+)-galanthamine and (+)-epigalanthamine was present, and used this to resolve racemic narwedine.

Shieh and Carlson, J. Org. Chem. (1994) 59: 5463, disclose crystallising racemic narwedine in the present of (+)-galanthamine from a solvent/amine base mixture, to give (−)-narwedine in good yield. They also disclose that seeding a solution of racemic narwedine in ethanol/triethylamine mixture with (−)-narwedine results in the crystallisation-induced asymmetric transformation of (−)-narwedine in 84% yield.

However, a problem with using the prior art processes for the resolution of narwedine on a large scale is that narwedine has a tendency to self-seed, sometimes giving material of poor enantiomeric excess, or even the opposite enantiomer of narwedine. For the purpose of industrial manufacture these factors compromise the reproducibility of the process.

The reduction of narwedine to galanthamine requires reagents that show 1,2- rather than 1,4 - regioselectivity, and that also give the required diastereoselectivity in the product, so that galanthamine is formed rather than epigalanthamine. There are several examples in the literature of reagents that favour the 1,2- reduction over the 1,4- reduction of enones and which can diastereo-selectively reduce the carbonyl function in the desired manner. Such examples include $LiAlH_4$ (see G. Schroder et al, Ber. (1971) 104: 3406; aluminium isopropoxide (seed. H. Picker et al, Syn. Comm. (1975) 5: 451); $NaBH_4$ with catalytic amounts of rare earth metal halides (see J. L. Luche, J. Am. Chem. Soc. (1978) 100: 2226 and M. M. Abelman et al, J. Am. Chem. Soc, (1990) 112: 6959); lithium aluminium tributoxy hydride (see H. Haubenstock, J. Org. Chem. (1972) 37: 656,); DIBAL (see K. E. Wilson et al, J. Chem. Soc., Chem Comm (1970), 213); REDAL (see C. Iwata et al, Chem. Pharm. Bull. (1988) 36: 14581); superhydride (see Y. Hitotsuyanagi et al, J. Chem. Soc., Chem Comm. (1994) 2707); and bulky trialkyl-borohydrides such as L-selectride (see W. G. Dauben et al, Tet. Lett. (1978) 4487 and A. M. P. Koskinen et al, Tet Lett. (1993) 34: 6765). Many of these reagents have been used for the reduction of narwedine and narwedine-type enones.

In particular, Barton and Kirby, J. Chem. Soc. (1962) 806, disclose that $LiAlH_4$ reduces narwedine regioselectively and with some diastereoselectivity to give galanthamine with contaminant epigalanthamine. Other workers have observed similar diastereoselectivity in this reaction; see T. Kametani et al, J. Chem. Soc. C (1969) 2602 and T. Kametani et al, J. Org. Chem. (1971) 36: 1295). Also Shieh and Carlson, in WO-A-9527715, disclose the use of $LiAlH_4$ /$AlCl_3$ to increase this diastereoselectivity.

Barton and Kirby (as above) also disclose that $NaBH_4$ is less regioselective than $LiAlH_4$ and obtain a mixture of 1,2- and 1,4- reduction products from narwedine, while Shieh and Carlson, in WO-A-9527715, disclose the use of the reagent $NaBH_4$/$CeCl_3$, known to be selective for 1,2-reduction over 1,4-reduction, to obtain galanthamine. $NaBH_4$ has also been found to give good diastereoselectivity on reduction of a highly substituted narwedine derivative to a galanthamine derivative; see K. Shimizu et al, Chem. Phar. Bull. (1973) 3765).

Shieh and Carlson, J. Org. Chem. (1994) 59: 5463, disclose the use of L-selectride to reduce narwedine to galanthamine without producing epigalanthamine. L-selectride has also been used to effect 1,2-reduction of the carbonyl function of N-formylbromonarwedine diastereoselectively, followed by $LiAlH_4$ to reduce the N-formyl group and remove the bromine to obtain galanthamine; see J. Szewczyk et al, J. Heterocyclic Chem. (1995) 32: 195.

SUMMARY OF THE INVENION

According to a first aspect of the present invention, a process for the asymmetric transformation of a racemic compound of formula (I), below (relative stereochemistry, shown), in which $R^1$ is H or an alkyl group having up to 20 carbon atoms, $R^2$ is H or an alkyl, aryl, alkaryl, aralkyl group having up to 20 carbon atoms, and X is H, a halogen, tert-butyl, or any other removable substituent, comprises reaction of racemic compound (I) with an enantiomerically-enriched acid HY*, wherein Y* is a chiral group, to form a diastereomeric salt of compound (I) having Y* as a counterion.

According to a second aspect of the present invention, a diastereomeric salt of compound (I) has as a counterion a chiral group Y* derived from an enantiomerically-enriched acid HY*.

Preferably, both $R^1$ and $R^2$ are, independently, an alkyl group having up to 4 carbon atoms, more preferably with one or both of them being methyl.

The crystallisation-induced asymmetric transformation of the present invention is advantageous over prior art entrainment procedures for a number of reasons. Firstly, the formation of the diastereomeric salt controls the stereochemistry of the product and eliminates any problem of self-seeding which may occur in entrainment procedures. This makes possible a dynamic one pot procedure, whereby all the substrate is converted into a single diastereomeric salt, giving a maximum theoretical yield of 100% instead of the normal 50% maximum yield from a normal classical resolution. This is unexpected, since in situ racemisation of narwedine-type compounds are reported to be catalysed by added base (see Shieh and Carlson, above), and yet in this dynamic process the racemisation occurs in the presence of a chiral acid.

Secondly, the process of the present invention is a general process for a range of compounds of the formula (I), not just for narwedine, provided that an appropriate acid is used as the resolving agent. Previous methods for resolution of narwedine rely on the fact that narwedine has a conglomerate crystal structure, and are therefore not general for other narwedine-type compounds which are not conglomerates.

Moreover, and also surprisingly, we have discovered that the diastereomeric salts produced by the process outlined above can be reduced directly to enantiomerically-enriched or enantiomerically-pure galanthamine without requiring the salt to be cracked.

According to a third aspect of the invention, therefore, a process for the preparation of a compound of formula (III), below (relative stereochemistry shown), comprises asymmetric transformation of a racemic compound of formula (I) using the process according to the first aspect of the invention, followed by reduction of the salt obtained.

This combined asymmetric transformation/reduction procedure represents a convenient and economical process for the preparation of enantiomerically-enriched or enantiomerically-pure galanthamine, or derivatives thereof.

DESCRIPTION OF THE INVENTION

The overall asymmetric transformation/reduction process is shown in Scheme 1, below. The invention is not limited to the stereochemistry shown.

The term asymmetric transformation is well understood in the art, and is defined, for example, in "Stereochemistry of Organic Compounds", Eliel and Wilen, 1994, John Wiley & Sons, Inc., p. 1192.

In the present invention, the required asymmetric transformation is achieved by treating the raceric form of compound (I) with an enantiomerically-enriched acid (HY*). The diastereomeric crystalline salt (II) of one enantiomer of compound (I) is essentially removed from solution by virtue of its insolubility, driving the equilibrium over to this form; for clarity, the salt is shown as having 1:1 stoichiometry, although in practice this may vary according to the molar ratio of reactants used. The crystalline diastereomeric salt (II) can then be reduced to an enantiomerically-enriched, or enantiomerically-pure, galanthamine-type compound of formula (III).

In the context of this Application, by enantiomerically-enriched we mean that one enantiomer of a chiral compound is present in an excess compared to the other enantiomer Typically, one enantiomer will be present in an excess of at least 70%, preferably at least 80%, and more preferably at least 90%, or higher, eg. at least 97%, compared to the other enantiomer. This term, therefore, is intended also to cover enantiomerically-pure, or single isomer, materials.

Any suitable acid may be used in the process of the present invention. The acid may be a mono-acid or a di-acid. When the acid is a mono-acid, typically the molar ratio of acid: compound (I) will be in the range 0.4–1.2: 1, preferably 1:1. Examples of suitable mono-acids include malic acid and abetic acid.

When a di-acid is used, typically the molar ratio of acid: compound (I) will be in the range 1.4–1.2:1, and preferably 1:1 or 0.5:1, depending upon whether a 1:1 salt or a 2:1 salt is required. Examples of suitable di-acids are derived from tartaric acid, with the preferred acid being di-toluoyltartaric acid.

For example, 0.5 mol equivalents of di-p-toluoyl-D-tartaric acid to 1 mol equivalent of narwedine is chosen if the 2:1 salt [(−)-narwedine]$_2$[di-p-toluoyl-D-tartrate] is required, and 1 mol equivalent of di-p-toluoyl-D-tartaric acid to 1 mol equivalent of narwedine is chosen if the 1:1 salt [(−)-narwedine][di-p-toluoyl-D-tartrate] is required.

Usually a substantially enantiomerically-pure acid will be used. Which enantiomer of chiral acid is chosen depends on which enantiomer of narwedine is required. For example, di-p-toluoyl-L-tartaric acid gives [(+)-narwedine]$_2$[di-p-toluoyl-L-tartrate] and di-p-toluoyl-D-tartaric acid gives [(−)-narwedine]$_2$[di-p-toluoyl-D-tartrate].

The asymmetric transformation is typically carried out in a solvent which is generally selected, but not exclusively, from methanol, ethanol,n-propanol, i-propanol, butanol, i-butanol, t-butanol, water, acetonitrile, dimethylformamide, tetrahydrofuran. Preferably the resolution is carried out in an alcoholic solvent, most preferably in ethanol, methanol or n-propanol.

The asymmetric transformation is generally carried out at a temperature up to the temperature of the refluxing solvent, typically above 20° C., preferably from 30 to 100° C., more preferably about 80° C., for up to 48 hours, preferably about 1 to 2 hours. The reaction mixture is then cooled to promote crystallisation of the salt, although typically the temperature remains above 20° C., preferably being from 30 to 80° C., more preferably from 40° C. to ambient temperature, and is typically held at that temperature for up to 24 hours. The diastereomeric salt which crystallises out can be isolated by filtration or centrifugation.

The diastereomeric salt can then be reduced to give enantiomerically-enriched or enantiomerically-pure compounds of formula (III), in good yield and substantially free of the epi-isomer thereof.

Surprisingly, it has been found that some reducing agents are selective enough for the carbonyl of narwedine that the acidic protons of the salt do not interfere with the reduction by quenching those reducing agents. Therefore, only one hydride equivalent of reducing agent per narwedine is required. Also, the acid resolving agent is not itself reduced, thereby allowing efficient recovery thereof. This renders the process of the invention highly economical, as such resolving agents tend to be expensive, putting it on a competitive footing with dynamic entrainment procedures in this respect. Unexpectedly we have also found that the diastereoselectivity of reduction with some reagents is greater on the salt than on free base form of compound (I).

Suitable reducing agents include L-selectride, K-selectride, N-selectride, LS-selectride, LiAlH$_4$, NaBH$_4$/CeCl$_3$, DIBAL and REDAL. L-selectride and LiAlH$_4$ are preferred. The amount of reducing agent used depends upon the salt to be reduced. Typically, 1 to 3 hydride equivalents are used per equivalent of narwedine.

The reduction is generally carried out at a temperature of from −100° C. to 40° C., preferably between −10° C. and 25° C., and most preferably at about 10° C., in a solvent generally selected from THF, toluene, dichloromethane, TBME, preferably THF. A suspension of the diastereomeric salt in the chosen solvent may be used, so that only a small volume of solvent (eg. 10 vol.) is necessary, rendering the process scaleable and economic. Normal work-up procedures can be utilized to give enantiomerically-enriched or enantiomerically-pure compounds of formula (III).

Preferably, the combined asymmetric transformation and reduction steps are designed to give compounds of formula (III) having the absolute stereochemnical configuration of (−)-galanthamine, allowing ready conversion to (−)-galanthamine. More preferably, the substrate for the resolution, compound (I), is selected to give (−)-galanthamine directly after the reduction step.

Advantageously, the reduction can be carried out in the same pot as the asymmetric transformation, without isolation of the diastereomeric salt.

The present invention is further illustrated by way of the following Examples.

EXAMPLES
Asymmetric Transformation

Example 1

Racemic narwedine (100 mg, 0.35 mmol) was dissolved in ethanol (3 ml) upon heating to reflux. Di-p-toluoyl-D-tartaric acid (58 mg, 0.17 mmol) was added and the mixture was cooled slowly to 40° C., maintained at this temperature overnight, then cooled to ambient temperature. The white solid was isolated by filtration to afford the 2:1 diastereomeric salt [(−)-narwedine]$_2$[di-p-toluoyl-D-tartrate] (79% yield, 98% e.e (−)-narwedine in salt).

Example 2

Di-p-toluoyl-D-tartaric acid (5.79 g, 14.99 mmol) was dissolved in ethanol (100 ml)on warming to 40° C. and then synthetic racemic narwedine (8.52 g,29.86 mmol) was added and the mixture was heated at reflux for 1 h then cooled to 40° C. and stirred for 16 hours at this temperature. The mixture was cooled to ambient temperature, stirred for 2 h and then the resultant white solid was isolated by filtration to give the 2:1 diastereomeric salt [(−)-narwedine]$_2$[di-p-toluoyl-D-tartrate] (11.86 g, 83% yield, 94% e.e.).

Example 3

The method described in Example 2 was repeated but with di-p-toluoyl-L-tartaric acid. The 2:1 diastereomeric salt [(+)-narwedine]$_2$[di-p-toluoyl-L-tartrate] (90% yield, 96% e.e.) was isolated.

Example 4

Racemic narwedine (100 mg, 0.35 mmol) was dissolved in ethanol (3 ml) on heating to reflux. Di-p-toluoyl-D-tartaric acid (58 mg, 0.17 mmol) was added then the reaction mixture was cooled to ambient temperature. The resulting white solid was isolated by filtration to afford the 1:1 diastereomeric salt [(−)-narwedine][di-p-toluoyl-D-tartrate] (90% yield, 98% e.e (−)-narwedine).

Example 5

Di-p-toluoyl-L-tartaric acid (1.35 g, 3.50 mmol) was dissolved in ethanol (10 ml) on heating to 40° C. and then synthetic racemic narwedine (1.00 g, 3.50 mmol) was added and the mixture was heated at reflux for 1 h then cooled to 40° C. and stirred for 16 hours at this temperature. The mixture was cooled to ambient temperature, stirred for 2 h and then the white solid was isolated by filtration to give the 1:1 diastereomeric salt [(+)-narwedine] [di-p-toluoyl-L-tartrate] (2.16 g, 92% yield, 96% e.e.).

Reduction

Example 6

To a suspension of [(−)-narwedine]$_2$[di-p-toluoyl-D-tartrate] (0.5 g, 0.52 mmol) in THF at room temperature, was added L-selectride (1M in THF, 1.14 ml, 1.14 mmol) and the reaction mixture was stirred for 30 minutes. The reaction was quenched with water (1 ml) and the solvent evaporated. The residue was partitioned between ethyl acetate (25 ml) and NaOH (2M, 25 ml). The aqueous phase was separated and acidified with HCl (conc) and di-p-toluoyl-D-tartaric acid was recovered as a white solid (85% yield). The organic phase was extracted by treatment with 2M HCl (2×10 ml) and washed with ethyl acetate. The remaining aqueous phase was basified by addition of solid potassium carbonate and the product was extracted into dichloromethane (2×10 ml). The combined organic phase was washed with brine, dried over magnesium sulfate, filtered and concerated, to afford (−)-galanthamine (91% yield, 94% e.e.).

Example 7

[(−)-Narwedine]$_2$[di-p-toluoyl-D-tartrate] (15.00 g, 14.63 mmol) was stirred in THF (140 ml, 14 vol) under nitrogen. The mixture was held at 12–13° C. in a water bath and L-selectride (1M in THF, 33 ml, 32.2 mmol, 1.1 eq per narwedine) was added dropwise over 30 minutes, then the solution was stirred at ambient temperature for 90 minutes. MeOH (1 ml) was added to quench the reaction and the solvent was removed in vacuo. The work-up procedure used was that described in Example 6, but scaled up.

(−)-Galanthamine was isolated as a white solid (6.11 g, 73% yield, 70% e.e) which was dissolved in ethanol (18 ml) and was treated with HBr (48%, 1.2 eq.). GalanthamineHBr precipitated out as a white solid and was isolated by filtration (7.8 g, 77% yield, >98% e.e).

Example 8

[(−)-Narwedine]$_2$[di-p-toluoyl-D-tartrate] (0.2 g, 0.21 mmol) was stirred in THF (5 ml) under nitrogen. The temperature was maintained at 0° C. then LiAlH$_4$ (1M in THF, 0.2 ml, 0.2 mmol) was added dropwise. The solution was stirred at ambient temperature for 30 minutes. The work-up procedure was as described in Example 6. A mixture of galanthamine and epigalanthamine (approximately 9:1 determined by $^1$H NMR) was isolated.

Scheme 1

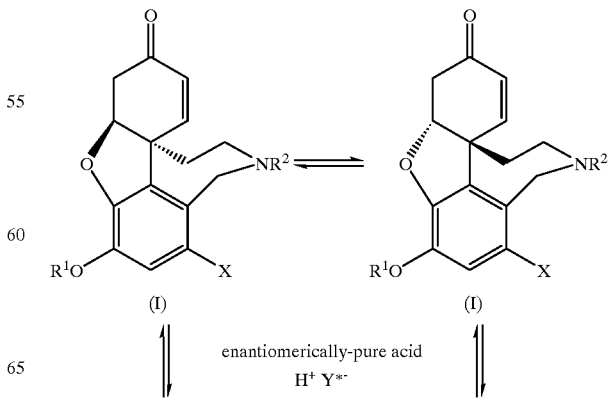

-continued

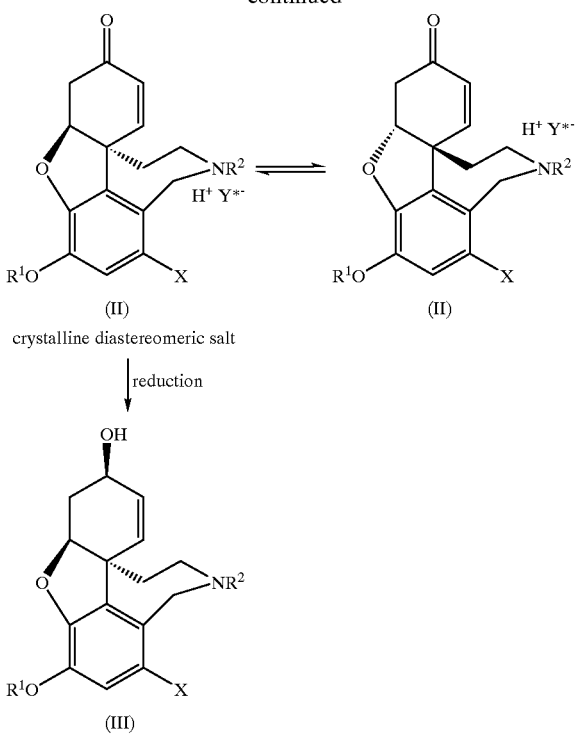

(II) crystalline diastereomeric salt ⇌ (II)

reduction (III)

What is claimed is:

1. A process for the production of an enantiomerically-enriched compound (III), comprising reduction of a diastereomeric salt of compound (I) having as a counterion a chiral group Y* derived from an enantiomerically-enriched monoacid HY*, wherein HY* is selected from the group consisting of abietic acid and malic acid, wherein compounds (I) and (III) have the following structures:

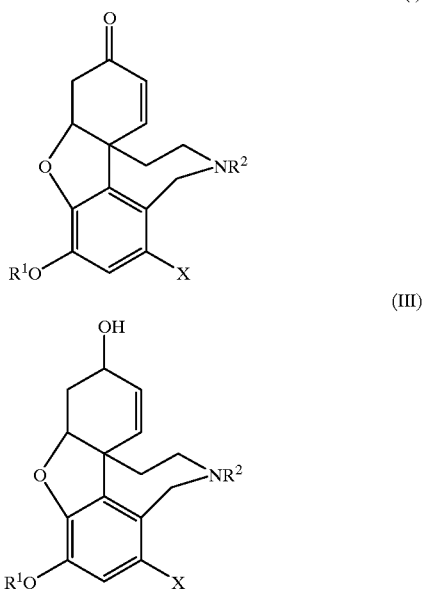

(I)

(III)

and $R^1$ is H or an alkyl group having up to 20 carbon atoms; $R^2$ is H, or is selected from the group consisting of alkyl, aryl, alkaryl, and an aralkyl group having up to 20 carbon atoms; and X is selected from the group consisting of H, a halogen atom, and tert-butyl.

2. The process, according to claim 1, which utilizes in said reduction a reducing agent selected from the group consisting of L-Selectride (lithium tri-sec-butyl borohydride), K-Selectride (potassium tri-sec-butyl borohydride), N-Selectride (sodium tri-sec-butyl borohydride), LS-Selectride (lithium trisamyl borohydride), $LiAlH_4$, $NaBH_4/CeCl_3$, DIBAL-H (di-isobutyl aluminum hydride), and RED-Al (bis(2-methoxyethoxy)aluminum hydride (>65 wt. % solution in toluene)).

3. The process, according to claim 2, where said reducing agent is L-Selectride (lithium, tri-sec-butyl borohydride).

4. The process, according to claim 1, wherein said salt is prepared by an asymmetric transformation comprising reaction of racemic compound (I) with an enantiomerically-enriched acid HY*.

5. The process, according to claim 4, which is a one pot process.

6. The process, according to claim 4, wherein after the reduction the acid HY* is recovered and recycled into the asymnmetric transformation step.

7. The process, according to claim 4, wherein the acid HY* used in the asymmetric transformation is in substantially single enantiomer form.

8. The process, according to claim 4, wherein compound (I) and the acid HY* are reacted together in a molar ratio of 0.4–1.2:1.

9. The process, according to claim 4, wherein the compound (I) and the acid HY* are reacted together in a solvent.

10. The process, according to claim 9, wherein the solvent is an alcohol solvent.

11. The process, according to claim 4, wherein compound (I) and the acid HY* are reacted together at a temperature above 20° C.

12. The process, according to claim 1, wherein compound (I) is narwedine.

13. The process, according to claim 1, wherein compound (III) has the same absolute configuration as (−)-galanthamine.

14. A diastereomeric salt of compound (I) having as a counterion a chiral group Y* derived from an enantiomerically-enriched acid HY*, where HY* is a chiral acid selected from the group consisting of di-toluoyl tartaric acid, abietic acid and malic acid wherein compound (I) has the following structure:

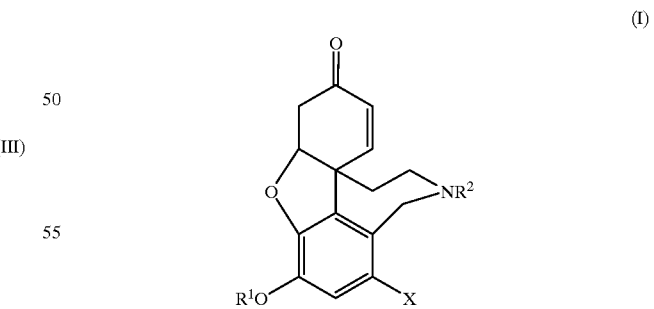

(I)

wherein $R^1$ is H or an alkyl group having up to 20 carbon atoms; $R^2$ is H, or is selected from the group consisting of alkyl, aryl, alkaryl, and an aralkyl group having up to 20 carbon atoms, and X is selected from the group consisting of H, a halogen atom, and tert-butyl.

15. The diastereomeric salt, accoeding to claim 14, wherein Y* is a counterion derived from an acid HY* wherein the acid HY* is derived from tartaric acid.

16. The diastereomeric salt, according to claim 15, wherein the said HY* is di-toluoyl tartaric acid.

17. A process for the production of an enantiomerically-enriched compound (III), comprising reduction of diastereomeric salt of compound (I) having as a counterion a chiral group Y* derived from an enantiomerically-enriched tartaric acid, wherein compounds (I) and (III) have the following structures:

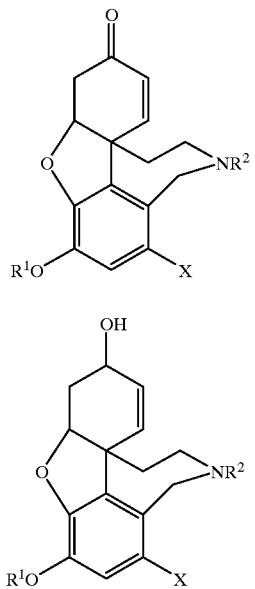

and $R^1$ is H or an alkyl group having up to 20 carbon atoms; $R^2$ is H, or is selected from the group consisting of alkyl, aryl, alkaryl, and an aralkyl group having up to 20 carbon atoms; and X is selected from the group consisting of H, a halogen atom, and tert-butyl.

18. The process, according to claim 17, wherein the tartaric acid is di-toluoyl tartaric acid.

19. The process, according to claim 17, which utilizes in said reduction a reducing agent selected from the group consisting of L-Selectride (lithium tri-sec-butyl borohydride), K-Selectride (potassium tri-sec-butyl borohydride), N-Selectride (sodium tri-sec-butyl borohydride), LS-Selectride (lithium trisamyl borohydride), LiAlH$_4$, NaBH$_4$/CeCl$_3$, DIBAL-H (di-isobutyl alumium hydride), and RED-Al (bis(2-methoxyethoxy) aluminum hydride (>65 wt. % solution in toluene)).

20. The process, according to claim 19, where said reducing agent is L-Selectride (lithium, tri-sec-butyl borohydride).

21. The process, according to claim 17, wherein said salt is prepared by an asymmetric transformation comprising reaction of racemic compound (I) with the enantiomerically-enriched tartaric acid.

22. The process, according to claim 21, which is a one pot process.

23. The process, according to claim 21, wherein after the reduction the tartaric acid is recovered and recycled into the asymmetric transformation step.

24. The process, according to claim 21, wherein the tartaric acid used in the asymmetric transformation is in substantially single enantiomer form.

25. The process, according to claim 21, wherein compound (I) and the tartaric acid are reacted together in a molar ratio of 1.4–1.2:1.

26. The process, according to claim 21, wherein the compound (I) and the tartaric acid are reacted together in a solvent.

27. The process, according to claim 26, wherein the solvent is an alcohol solvent.

28. The process, according to claim 21, wherein compound (I) and the tartaric acid are reacted together at a temperature above 20° C.

29. The process, according to claim 17, wherein compound (I) is narwedine.

30. The process, according to claim 17, wherein compound (III) has the same absolute configuration as (−)-galanthamine.

* * * * *

UNITED STATES PATENT AND TRADEMARK OFFICE
CERTIFICATE OF CORRECTION

PATENT NO. : 6,346,618 B1
DATED : February 12, 2002
INVENTOR(S) : David Andrew Chaplin, Nicholas Bernard Johnson, Gerard Andrew Potter and Jane Marie Paul It is certified that error appears in the above-identified patent and that said Letters Patent is hereby corrected as shown below:

Column 8,
Line 3, "accordingto" should read -- according to --.
Line 12, "process,according" should read -- process, according --.
Line 21, "asymnmetric" should read -- asymmetric --.

Signed and Sealed this

Twenty-third Day of April, 2002

Attest:

Attesting Officer

JAMES E. ROGAN
Director of the United States Patent and Trademark Office